United States Patent [19]

Nowak, Jr. et al.

[11] 3,972,336

[45] Aug. 3, 1976

[54] HAIR FIXATIVES BASED ON SULFONATED STYRENE POLYMERS

[75] Inventors: Frank A. Nowak, Jr., Bound Brook; Frank Theodore Koehler, Jr., Plainfield, both of N.J.

[73] Assignee: National Starch and Chemical Corporation, Bridgewater, N.J.

[22] Filed: Apr. 18, 1975

[21] Appl. No.: 569,358

Related U.S. Application Data

[63] Continuation-in-part of Ser. No. 451,175, March 14, 1974, abandoned, and a continuation-in-part of Ser. No. 288,530, Sept. 13, 1972, abandoned.

[52] U.S. Cl. .................................... 132/7; 8/127.51; 424/DIG. 1; 424/DIG. 2; 424/47; 424/70; 424/71; 424/78; 424/81
[51] Int. Cl.² .......................................... A45D 7/04
[58] Field of Search ................. 424/DIG. 1, DIG. 2, 424/47, 70, 71, 78, 81; 8/127.51; 132/7; 260/79.3 R, 503, 505, 686

[56] References Cited
UNITED STATES PATENTS

| 2,533,210 | 12/1950 | Baer | 260/686 |
|---|---|---|---|
| 2,638,445 | 5/1953 | Young et al. | 260/79.3 R |
| 2,669,557 | 2/1954 | Wheaton | 260/79.3 R |
| 2,764,576 | 9/1956 | Blaser et al. | 260/79.3 R |
| 3,072,618 | 1/1963 | Turbak | 260/79.3 R |
| 3,377,250 | 4/1968 | Hansen | 424/70 |
| 3,577,517 | 5/1971 | Kubot et al. | 424/47 |
| 3,579,632 | 5/1971 | Sonnen | 424/70 |
| 3,634,022 | 1/1972 | Robbins et al. | 8/127.51 |
| 3,723,375 | 3/1973 | Field et al. | 424/70 X |
| 3,726,288 | 4/1973 | Nowak et al. | 424/71 X |

*Primary Examiner*—Leonard Schenkman
*Assistant Examiner*—Vera C. Clarke
*Attorney, Agent, or Firm*—Thomas B. Graham

[57] ABSTRACT

A process for setting hair is disclosed comprising the steps of applying to the hair a solution of sulfonated polymer selected from the group consisting of sulfonated polystyrene, sulfonated interpolymers of styrene and ethylenically unsaturated comonomers, and soluble salts of said sulfonated polymers, setting the hair in the desired configuration, and allowing the hair to dry while it is retained in the desired configuration.

8 Claims, No Drawings

3,972,336

HAIR FIXATIVES BASED ON SULFONATED STYRENE POLYMERS

REFERENCE TO RELATED APPLICATIONS

This application is a continuation-in-part of U.S. Ser. No. 451,175, filed Mar. 14, 1974, now abaondoned, which is a continuation-in-part of U.S. Ser. No. 288,530, filed Sept. 13, 1972, now abandoned.

BACKGROUND OF THE INVENTION

This invention relates to a process for setting hair in a desired configuration, and more particularly to hair setting processes using an aqueous, alcoholic or aqueous-alcoholic solution of a sulfonated polymer which serves as a hair fixative.

A common type of hair setting preparation comprises an aqueous or aqueous-alcoholic lotion or gel containing a film forming material which is applied to the hair, which is then fixed in the desired configuration and allowed to dry. The film forming material or fixative is deposited on the individual hair filaments in the form of a microscopically thin layer which encases the hair filaments and by reason of its resistance to deformation tends to keep the hair in the configuration in which it has been set. Likewise, at places where the hair filaments cross or touch one another, the dried fixative acts as an adhesive and binds the hair filaments together, thus helping to hold the proper set. Furthermore, the presence of the fixative film on the hair also imparts desirable properties such as body and smoothness.

In order to be effective, the film forming ingredients of a hair setting composition must meet a number of rigid requirements. Thus, the films derived from these ingredients should be flexible and yet they should possess strength and elasticity; they should display good adhesion to hair so as to avoid dusting or flaking off with the passage of time or when the hair is subjected to stresses; they should not interfere with the combing and brushing of the hair; they should remain free of tackiness or gumminess under humid conditions; they should be clear, transparent, and glossy, and maintain their clarity on aging; they should maintain good antistatic properties; and, they should be easily removable by washing with water and either a soap or shampoo.

Natural gums, such as quince-seed and karaya gums, have been used as fixatives in hair setting lotions, but because of the disadvantages associated with such gums, e.g., variability from lot to lot, they have been generally replaced by synthetic film-forming materials. Thus, polyvinyl alcohol, polyvinylpyrrolidone, cellulose ethers such as methyl cellulose, and copolymers of vinyl-pyrrolidone and vinyl acetate, have been used as fixatives in hair setting lotions and gels.

SUMMARY OF THE INVENTION

It is an object of this invention to provide hair setting compositions which exhibit all of the above described properties. It is a further object of this invention to provide film forming polymeric components for such compositions which are soluble in aqueous, alcoholic and aqueous-alcoholic hair setting lotions and are utilizable with halogenated hydrocarbons and other compounds ordinarily employed as aerosol propellants in aqueous systems. This combination of properties makes these polymeric components particularly useful in hairdressing processes according to this invention.

These and various other objects and advantages of this invention will become apparent to the practitioner from the following detailed description thereof.

We have now discovered that all of the previously described requirements for an effective hair setting formulation are met by utilizing aqueous, alcoholic or aqueous-alcoholic solutions of sulfonated polystyrene or sulfonated interpolymers of styrene ans ethylenically unsaturated comonomers, or the partially and fully neutralized salts of these sulfonated polymers.

The hair setting process of this invention comprises the steps of applying to the hair a preparation comprising a solution of a sulfonated polystyrene homopolymer or interpolymer, or salt thereof, setting the hair in the desired configuration, and allowing the hair to dry while it is held in the desired configuration.

DESCRIPTION OF THE PREFERRED EMBODIMENTS

The hair setting compositions employed in the process of this invention are aqueous, alcoholic or aqueous-alcoholic solutions of sulfonated polystyrene based polymers. Two different types of sulfonated polymers are useful. The first type is a sulfonated homopolymer of styrene. The second type is a sulfonated interpolymer of styrene with an ethylenically unsaturated comonomer. The useful compounds include the partially or fully neutralized salts of either the sulfonated polystyrene or the sulfonated styrene interpolymers, i.e. the soluble salts of either the sulfonated polystyrene or the sulfonated styrene interpolymer wherein the sulfonic acid groups are partially or fully neutralized.

In general, the method for preparing the hair setting compositions of this invention merely involves admixing the film forming, sulfonated polymeric hair fixative with the selected solvent, adding any modifying agents, if desired, and thereupon thoroughly mixing the ingredients to obtain a homogeneous system.

In general, the method for preparing the aerosol type compositions contemplated herein merely involves combining the selected aerosol propellant with the hair setting formulation comprising the mixture of sulfonated polymer with a suitable solvent.

In the preparation of the hair setting compositions herein having alcoholic or aqueous-alcoholic solvents, low molecular weight cosmetically acceptable alcohols, e.g., ethanol, or isopropanol may be used. In any instance the amount of alcohol used is regulated so as to effect the desired volatilization range and solubility of perfume oils and other optional, organic substances. Any aqueous-alcoholic mixtures in which the polymer is completely soluble may be used. Preferred mixtures are those containing 50 percent or less of alcohol, by weight, of the total solvent.

Since the use of isopropanol often presents odor problems it is preferred that denatured ethanol be utilized in the aqueous-alcoholic systems in amounts ranging from about 10 to about 40 percent, by weight, of the total solvent.

Among the various ethylenically unsaturated vinyl type comonomers which may be copolymerized with styrene to make the interpolymers suitable for sulfation are included, i.e., the acrylic and methacrylic esters of aliphatic alcohols such as methyl, ethyl, butyl, and 2-ethyl hexyl alcohols; acrylic acid; acrylonitrile; methacrylonitrile; dibutyl maleate; vinylidene chloride; N-vinyl pyrrolidone; etc. Any of these and other monomers which possess the characteristic, functional —CH=CH— group which copolymerizes with the styrene, yet is otherwise inert or at least will not appreciably interfere with subsequent sulfonation of the styrene units, may be used to make the interpolymers with styrene contemplated in this invention. Preferred interpolymers will be prepared using styrene in a proportion of at least 50 percent, by weight.

With regard to the preparation of the sulfonated polystyrenes and interpolymers described hereinabove, the base polymers may be synthesized by any conventional method, and the sulfonating of the parent compound may be carried out according to the method taught in U.S. Pat. No. 3,072,618, A. F. Turbak, Jan. 8, 1963. using phosphorus compound-sulfur trioxide adducts.

The base homopolymers and interpolymers herein can be prepared by means of bulk suspension, solution or emulsion polymerization techniques, or by any other suitable means. The sulfonated derivatives of these polymers useful in the practice of this invention may have average molecular weights between 6,000 and 7,000,000, preferably between 80,000 and 500,000. These sulfonated derivatives of styrene homo- and interpolymers upon utilization in accordance with this invention are all characterized by their ability to display desirable hair fixing properties.

The hair setting preparations used in the process of this invention are prepared by dispersing the sulfonated polymer, preferably in the form of a finely divided powder, in the solvent with vigorous agitation. In one embodiment, a solution of a basic compound such as sodium hydroxide or ammonium hydroxide or sodium carbonate is then added while stirring is continued. Adding the basic compound ionizes the sulfonic acid groups of the unneutralized polymer.

The neutralizing base and quantity to be used should be chosen to produce a polymer which yields a solution pH which will not damage the hair or irritate the skin. A preferred solution pH range is 4.0 to 8.0. Useful neutralizing bases include sodium hydroxide, potassium hydroxide, sodium carbonate, ammonia, ethanolamine, diethanolamine, triethanolamine, isopropanolamine, diisopropanolamine, triisopropanolamine, 2-amine-2-methyl-1-propanol, 2-amino-2-methyl-1,3 propanediol, and the like, and mixtures thereof.

The concentration of polymer used in the hair setting preparation of this invention may vary from 0.1% to 10.0%, by weight. The maximum usable concentration will depend on the nature and molecular weight of the polymer, the degree of neutralization, the neturalizing agent used, and the solvent system chosen, as will be understood by those skilled in the art.

With regard to proportions, the final hair setting compositions typically contain a salt of either a sulfonated polystyrene or a sulfonated interpolymer of styrene as the hair fixative agent in a concentration ranging from about 0.5 to 3.0 percent, by weight; the solvent, whether aqueous, alcoholic or aqueous-alcoholic, may be in a concentration ranging from about 97 to 99.5 percent, by weight of the total composition.

In the practice of this invention, it is preferred that sodium salts of the sulfonated polymers having molecular weights between about 80,000 and 500,000 be used as the hair fixatives in water at a concentration ranging from about 0.5 to about 3.0 percent, by weight of the total solution.

In the instance of the aerosol type compositions, various propellants, which are well known to those skilled in the art, may be used. For instance, the commonly used propellants include dichlorotetrafluoroethane, dichlorofluoromethane, isobutane, and propane, etc., as well as suitable combinations thereof. The aerosol compositions will contain typically from about 7 – 90 percent, by weight, of solvent and from about 10 – 90 percent, by weight, of propellant. These proportions are to be considered merely illustrative inasmuch as it may be possible to prepare some compositions using solvent or propellant outside of these ranges. Practitioners in the art will be able to determine the necessary (effective) amount for specific formulations without difficulty. It is preferred that the aerosol spray conditioners use sulfonated polymers having average molecular weights no greater than about 300,000.

In preparing the compositions in the form of quick breaking foams an emulsifying agent (or a compound having an emulsifying function) is necessary, ordinarily in amounts ranging from about 0.05 to 5%. Again, practitioners will be able to determine the precise amount necessary for specific formulations without difficulty.

Since the sulfonated polystyrenes tend to support bacterial growth, a small amount of a preservative should be added to prevent any microbial growth. Though other well known preservatives such as the lower molecular weight alkyl-p-hydroxybenzoates may be employed, we prefer to use formaldehyde.

Optional additives may be incorporated into the hair setting compositions of this invention in order to modify certain properties thereof. Among these additives may be included: placticizers such as glycols, esters and glycerine; emollients, lubricants, and lanolin compounds, protein hydrolyzates and other protein derivatives, ethylene oxide adducts, and cholesterol derivatives; dyes and other colorants, perfumes, and ultraviolet light absorbers. The polymeric fixative agents show little or no tendency to react with such additives.

The resulting hair dressing formulations exhibit all of the characteristics required of such a product. Their films are transparent, glossy, flexible and strong. They possess good antistatic properties, adhere well to hair, are easily removed by soapy water or shampoos, allow the hair to be readily recombed, and do not become tacky when exposed to high humidities. In addition, it should be noted that the resin solutions of this invention remain effective in holding the hair when optional conventional ingredients are incorporated therein in either the aqueous or aqueous-alcoholic solvent based formulations.

The hair setting procedure used in practicing this invention is entirely conventional. Ordinarily the hair is wetted; the setting preparation is applied and combed through for even distribution, the hair is fixed in the desired configuration and allowed to dry while it is held in this configuration. The hair is then combed out into the desired set. Variations from this procedure may be known to those skilled in the art and may be introduced without departing from the scope of this invention.

The invention will now be further illustrated by, but is not intended to be limited to, the following examples. The quantities of all ingredients are given in parts, by weight, of the total formulation.

EXAMPLE I

This example illustrates the usefulness of a sulfonated polystyrene as a fixative in a hair setting composition of this invention.

The following ingredients were introduced into a vessel equipped with means for mechanical agitation:

| | Parts |
|---|---|
| Sulfonated polystyrene sodium salt (av. m.w. = approx. 500,000) | 2.0 |
| Water (deionized) | 98.0 |
| Formaldehyde (preservative at 37% solution) | 0.1 |

Under agitation, the above ingredients were thoroughly mixed for about 30 minutes, whereupon the resulting solution was evaluated for its utility as a hair fixing formulation according to the test procedure set forth hereinafter. Conclusions based on observations were as follows:

The product of the test sample was a clear homogeneous solution. When applied to several swatches of hair and dried, it deposited a glossy, non-tacky film in each instance. Also, it was observed that the test composition rendered the hair more manageable than that which was not treated. This was evidenced by the fact that it served to hold the hair in the desired configuration while allowing for its recombing.

Curl Retention Properties — The ability of the hair setting compositions herein to retain a curl is determined in the following manner:

Clean swatches of European human hair, each averaging about 10 inches in length and weighing approximately 2 grams, were suspended from a horizontal bar and wet with water.

Equal quantities of the hair setting composition to be evaluated were then uniformly applied to the swatches and evenly distributed by combing the swatches. Observations of the tendency to tangle or snarl were recorded. Snarled hair could not, of course, be easily combed. Each composition tested was rated as either poor, fair, good, or excellent with repsect to its wet combing properties. The combed, wet swatch was next wound on a polytetrafluoroethylene mandrel having a one-half inch diameter, after which the mandrel was removed while the curl was secured with a clip. The thus treated curl was dried at 140°F. for about 30 minutes and then conditioned for 16 hours at 72°F. and a relative humidity of 50 percent.

After the conditioning period was completed, the clip was removed, and the curl was unwound into a helical configuration. The curl was measured for initial length ($L_o$) and then placed in a cabinet wherein the temperature was maintained at 72°F. and the relative humidity at 90 percent. The length of the curl was recorded at 30 minute intervals over a period of 120 minutes. The following formula was used to calculate the percent curl retention:

$$\text{Per Cent Curl Retention} = \frac{(L-L_t)}{(L-L_o)} \times 100,$$

wherein $L$ = length of fully extended hair, $L_o$ = length of hair before exposure to 90 percent relative humidity, $L_t$ = length of hair (at time $t$) after exposure to 90 percent relative humidity In the latter evaluation, a standard hair setting composition having an equal amount of a carboxylated polyvinyl acetate copolymer (about 82% neutralized with 2-amino, 2-methyl, 1-propanol fixative, in lieu of the salt of the sulfonated polystyrene, was used as a control. Herein a series of nine samples each for the test solution and the control were similarly treated and simultaneously tested.

Mean percent curl retention results compared as follows:

| Sample | Exposure Time | |
|---|---|---|
| | 30 min. | 120 min. |
| Control | 51.1% | 39.7% |
| Test solution | 66.9% | 56.6% |

As indicated above, the test solution proved to be a superior hair setting composition over the control. Furthermore, it was as readily removable from the hair by the use of a conventional shampoo.

EXAMPLE II

This example illustrates the usefulness of a hair setting composition utilizing an aqueous-alcoholic solvent and a sulfonated interpolymer typical of this invention.

In this instance, the interpolymer was prepared by reacting 70 parts of styrene with 30 parts of methyl methacrylate. The reaction was continued until a polymer having a molecular weight of about 300,000 was obtained. Sulfonation of the interpolymer was carried out in a manner according to that of the method employed in Example I of U.S. Pat. No. 3,072,618, A. F. Turbak, Jan. 8, 1963. A sufficient quantity of this sulfonated polymer was used to make up a test solution while a sulfonated polystyrene similar to that in Example I was employed as a control. The formulation described below was prepared and tested for hair setting ability utilizing the procedure set forth in Example I hereinabove.

| Ingredient | Parts |
|---|---|
| Sodium salt of the sulfonated interpolymer | 2.0 |
| Water (deionized) | 68.0 |
| Ethanol (denatured) | 30.0 |

The clarity of the solution was excellent, and the percent curl retention results were comparable to those obtained with the product prepared in Example I.

EXAMPLE III

This example illustrates the usefulness of a sulfonated polystyrene in the preparation of a hair dressing composition using an aqueous-alcoholic solvent according to this invention.

In addition to the test compositions a series of controls each having a particular conventional, polymeric hair fixative agent therein were prepared.

The formulations described in the table below were all prepared and tested utilizing the procedures set forth in Example I, hereinabove.

| Formulations | Sample No. and Parts in Each | | | | | |
|---|---|---|---|---|---|---|
| | 1 | 2 | 3 | 4 | 5 | 6 |
| Sulfonated polystyrene sodium salt (m.w. = 500,000) | 2.0 | — | — | — | — | — |
| Polyvinyl pyrrolidone | — | 2.0 | — | — | — | — |
| 30 parts vinyl pyrrolidone/ 70 parts vinyl acetate copolymer (50% alcoholic solution) | — | — | 4.0 | — | — | — |
| Vinylmethyl ether/monobutyl maleate copolymer (50% solution) | — | — | — | 4.0 | — | — |
| Carboxylated polyvinyl acetate copolymer | — | — | — | — | 2.0 | — |
| 70 parts vinyl pyrrolidone/ 30 parts vinyl acetate copolymer (50% solution) | — | — | — | — | — | 4.0 |
| Water (deionized) | 88.00 | 88.00 | 86.00 | 75.80 | 77.75 | 71.00 |
| 2-Amino-2-methyl-1,3-propanediol | — | — | — | 0.20 | 0.25 | — |
| Denatured ethanol (anhydrous) | 10.0 | 10.0 | 10.0 | 20.0 | 20.0 | 25.0 |

The results of the hair setting ability tests were as follows:

| Sample No. | Mean % Curl Retention | |
|---|---|---|
| | 30 min. | 120 min. |
| 1 | 59.1 | 48.1 |
| 2 | 26.0 | 19.3 |
| 3 | 34.8 | 25.1 |
| 4 | 44.4 | 33.3 |
| 5 | 35.6 | 27.3 |
| 6 | 31.8 | 20.6 |

The data summarized above serves to illustrate the improved hair setting ability of the polystyrene sulfonate salt employed in sample 1, over the control formulations.

EXAMPLE IV

This example illustrates the excellent hair setting ability exhibited by a variety of partially and fully neutralized polystyrene sulfonate salts utilized in preparing the products of this invention. It further illustrates the usefulness of various neutralizing agents.

The procedural steps of Example I were repeated in the preparation and testing of a series of hair setting compositions having the following formulations:

| Formulation | Sample No. and Parts in Each | | | | | | | |
|---|---|---|---|---|---|---|---|---|
| | 7 | 8 | 9 | 10 | 11 | 12 | 13 | 14 |
| Sulfonated polystyrene (acid form with av. m.w. approx. 500,000) | 2.0 | 2.0 | 2.0 | 2.0 | 2.0 | 2.0 | 2.0 | 2.0 |
| Water (deionized) | 97.52 | 97.04 | 97.48 | 97.96 | 96.78 | 97.57 | 97.67 | 97.35 |
| 2-amino-1-methyl,1-propanol | 0.48 | 0.96 | — | — | — | — | — | — |
| 2-amino-2-methyl-1,3-propanediol | — | — | 0.52 | 1.04 | — | — | — | — |
| Sodium Hydroxide | — | — | — | — | 0.22 | 0.44 | — | — |
| Ammonium Hydroxide (conc.) | — | — | — | — | — | — | 0.33 | 0.66 |
| Formaldehyde (37% soln. preservative) | 0.10 | 0.10 | 0.10 | 0.10 | 0.10 | 0.10 | 0.10 | 0.10 |
| Per cent neutralization | 50 | 100 | 50 | 100 | 50 | 100 | 50 | 100 |

The solutions were clear and yielded the following respective curl retention test results:

| % Curl Retention | Sample No. | | | | | | | |
|---|---|---|---|---|---|---|---|---|
| | 7 | 8 | 9 | 10 | 11 | 12 | 13 | 14 |
| at 30 minutes | 64.2 | 61.4 | 61.0 | 55.0 | 40.8 | 43.0 | 64.0 | 64.6 |
| at 120 minutes | 47.1 | 41.3 | 39.7 | 35.1 | 29.3 | 33.2 | 52.9 | 50.2 |

The data summarized above illustrates that the partially neutralized sulfonated polystyrene solutions are as readily applicable for the purposes of this invention as those which are fully neutralized.

EXAMPLE V

This example illustrates the unique applicability of a polystyrene sulfonate salt hair fixative in an aerosol type quick breaking hair setting foam according to this invention.

In this example, there was incorporated into the formulation, in addition to the propellant, a small amount of a conventional emulsifying agent. The aerosol quick breaking foam formulation comprised as the following:

|  | Formulation | Parts |
|---|---|---|
| Concentrate: | Sulfonated polystyrene sodium salt (20% solution) | 7.50 |
|  | Water (deionized) | 42.40 |
|  | Ethoxylated fatty alcohol emulsifying wax | 0.10 |
|  | Denatured ethanol (anhydrous) | 35.00 |
| Propellant: | 90/10 blend of isobutane and propane | 15.00 |

Upon adequate stirring to ensure homogeneity throughout the concentrate, it was observed that the solution was free of any precipitation. The concentrate and the propellant were then charged separately into an aerosol container. The resulting foam formulation was tested for its usefulness and compared with a commerical aerosol quick breaking foam.

When utilized, the hair setting composition deposited a film which was characterized by its gloss, softness and flexibility.

Curl retention results based on the standard test set forth hereinabove were comparable to those of the composition employed in Example I. Furthermore the present hair setting composition, when dried, was also readily removed from the hair by the use of a conventional shampoo.

EXAMPLE VI

This example illustrates the usefulness of a polystyrene sulfonate salt as a hair fixative in an aerosol, spray type conditioner for setting hair according to this invention.

The formulation of the test composition was as follows:

|  | Ingredient | Parts |
|---|---|---|
| Concentrate: | Water (deionized) | 42.0 |
|  | Sulfonated polystyrene sodium salt (av. m.w. approx. 80,000) | 1.0 |
|  | Ethanol (denatured) | 42.0 |
| Propellant: | Isobutane | 15.0 |

The ingredients making up the concentrate were charged into a suitable container and thoroughly mixed. Then the homogeneous concentrate and the propellant were separately charged into an aerosol container.

When utilized, the sprayed hair setting composition imparted the desired gloss and flexibility to the hair swatches. Curl retention test results based on the standard test described in Example I were comparable to those obtained in that same example. Similarly, the spray type hair setting composition herein, when dried, was readily removed from the hair by the use of a conventional shampoo.

EXAMPLE VII

This example illustrates a hair fixing composition using a polystyrene sulfonate having a different molecular weight.

A hair fixing formulation having the following composition was prepared and evaluated by the procedures of Example I.

| Ingredient | Parts Sample | Control |
|---|---|---|
| Polystyrene sulfonate (sodium salt) (avg. mol. wt. = 70,000) | 2.0 | x |
| Polyvinyl pyrrolidone | x | 2.0 |
| Water (deionized) | 97.9 | 97.9 |
| Preservative (37% formaldehyde solution) | 0.1 | 0.1 |
|  | 100.0 | 100.0 |
| Mean % Curl Retention at 30 min. | 43.0% | 27.5% |
| at 120 min. | 31.9% | 21.5% |

The results show that the test formulation is superior to the control. The test formulation rendered the hair glossy and free of static electricity, and was easily removed from the hair with a conventional shampoo.

EXAMPLE VIII

This example illustrates a hair fixing composition using a polystyrene sulfonate having a different molecular weight.

A hair fixing formulation having the following composition was prepared and evaluated by the procedure of Example I.

| Ingredients | Sample | Parts Control 1 | Control 2 |
|---|---|---|---|
| Polystyrene sulfonate (sodium salt) (avg. mol. wt. = 130,000) | 2.0 | x | x |
| Polyvinyl pyrrolidone | x | 2.0 | x |
| 70 parts vinyl pyrrolidone/ 30 parts vinyl acetate copolymer (50% solution) | x | x | 4.0 |
| Water (deionized) | 78.0 | 78.0 | 76.0 |
| Ethanol | 20.0 | 20.0 | 20.0 |
|  | 100.0 | 100.0 | 100.0 |
| Mean % Curl Retention at 30 min. | 38.2% | 24.4% | 36.3% |
| at 120 min. | 27.7% | 17.7% | 19.3% |

The results show that the test solution is superior to the controls. The test formulation rendered the hair glossy and free of static electricity, and was easily removed with a conventional shampoo.

EXAMPLE IX

This example illustrates hair fixing compositions using sulfonated polystyrenes of different molecular weights.

Hair setting formulations were prepared by adding sulfonated polystyrenes of different molecular weights, as specified in the formulas below to water with vigorous agitation.

| Ingredients | Parts | |
|---|---|---|
| | 1 | 2 |
| Polystyrene sulfonate (sodium salt) (Avg. M.W. = 6,000) | 10.0 | x |
| Polystyrene sulfonate (sodium salt) (Avg. M.W. = 7,000,000) | x | 0.1 |
| Water (deionized) | 89.9 | 99.8 |
| Preservative (37% formaldehyde) (solutions) | 0.1 | 0.1 |
| | 100.0 | 100.0 |
| Viscosity (RVF. Brookfield/72°F/20 RPM) | 40 cps | 90 cps |

The formulations were lubricious solutions which when applied to human hair provided excellent wet and dry combing properties, sheen, and antistatic properties. Each was effective in fixing the hair in a desired configuration.

EXAMPLE X

This example illustrates the use of a polystyrene sulfonate having a lithium cation.

Hair fixing formulations were prepared having the following compositions, and evaluated according to the procedures of Example I.

| Ingredients | | Parts | |
|---|---|---|---|
| | | 1 | 2 |
| Polystyrene sulfonate (lithium salt) (Avg. M.W. = 60,000) | | 2.0 | x |
| Polystyrene sulfonate (sodium salt) (Avg. M.W. = 130,000) | | x | 2.0 |
| Water (deionized) | | 58.0 | 58.0 |
| Ethanol | | 40.0 | 40.0 |
| | | 100.0 | 100.0 |
| Mean % Curl Retention | 30 minutes | 80.7% | 77.2% |
| | 120 minutes | 66.9% | 62.5% |

The results show that the polystyrene sulfonate having a lithium cation was as effective a hair fixative as the polystyrene sulfonate having a sodium cation.

EXAMPLE XI

This example illustrates a hair dressing formulation having a relatively high concentration of alcohol in the solvent.

A hair dressing formulation was prepared having the following composition.

| Ingredients | Parts |
|---|---|
| Polystyrene sulfonate (lithium salt) (Avg. M.W. = 60,000) | 2.0 |
| Water (deionized) | 20.0 |
| Ethanol | 78.0 |
| | 100.0 |

The formulation was found to be a satisfactory hair fixative in all aspects.

EXAMPLE XII

This example illustrates the use of the unneutralized polystyrene sulfonic acid as a hair fixative.

Hair fixing formulations were prepared having the following compositions.

| Ingredient | Parts | |
|---|---|---|
| | 1 | 2 |
| Polystyrene sulfonic acid (Avg. M.W. = 70,000) | 2.0 | 2.0 |
| Ethanol | 98.0 | x |
| Water (deionized) | x | 98.0 |
| | 100.0 | 100.0 |
| Mean % Curl Retention at 30 minutes | 53.9% | |
| at 120 minutes | 48.0% | |

When evaluated, the compositions of this example were found to have satisfactory hair fixing properties.

EXAMPLE XIII

This example illustrates the use of various sulfonated copolymers of styrene as hair fixatives.

Several styrene copolymers were prepared by the following procedure. A 70 percent monomer solution in 1,2-dichloroethane was prepared by dissolving styrene and a comonomer in the chosen proportions. The solution was heated to 125°C. and a total of 1 percent of benzoyl peroxide, based on the weight of the monomers, was slowly added as a dilute solution in 1,2-dichloroethane over a period of 4 hours. The mixture was heated for 2 additional hours, at which time the polymerization was complete. The copolymers were then sulfonated by the procedure of Turbak, U.S. Pat. No. 3,072,618. Hair setting formulations were prepared having the compositions in Table I below and tested by the procedures of Example I.

All formulations were found to have good hair holding properties and imparted to the hair good gloss. They also showed adequate resistance to flaking when the hair was combed.

The polystyrene bases were commercially prepared by the polymerization of styrene obtained by reacting benzene and ethylene. The reaction which is a three stage operation involving alkylation, dehydration, and purification, is described in the R. E. Kirk — D. F. Othmer Encyclopedia of Chemical Technology 2nd Edition, 13, 122, 134, and 146–179.

The styrene and methyl methacrylate interpolymer was also a commerical product prepared by separately charging the two monomers into a reaction vessel and reacting said monomers in an inert atmosphere in the presence of heat and a catalyst.

Polymers having desired average molecular weights can be prepared by closely controlling reaction conditions. The average molecular weights of the polymers described above may be determined by the intrinsic viscosity method outlined by C. S. Marvel in "An Introduction To The Organic Chemistry of High Polymers", 1959, pages 6–8.

Summarizing, it is thus seen that this invention provides a novel process for setting hair using lotions, aerosol foam and aerosol spray type formulations characterized by their ability to provide a glossy film having excellent hold power, when applied to the hair, and their ability to be readily removable therefrom upon the use of conventional shampoo. In addition to these outstanding properties, the hair setting compositions herein provide unusually good curl retention in high humidity as well as under normal conditions, remarkable adhesion to hair during brushing, and good antistatic properties.

Variations may, of course, be made in proportions, procedures, and materials without departing from the scope of this invention which is defined by the following claims.

TABLE I

| Ingredient | A | B | C | D | E | F | G | H | I |
|---|---|---|---|---|---|---|---|---|---|
| | | | | | Parts | | | | |
| [sulfonated (50 styrene/50 t-butyl styrene)] sodium salt | 2.0 | x | x | x | x | x | x | x | x |
| [sulfonated (90 styrene/10 N-vinyl pyrollidone)] sodium salt | x | 2.0 | x | x | x | x | x | x | x |
| [sulfonated (95 styrene/5 t-butyl aminoethyl methacrylate)] sodium salt | x | x | 2.0 | x | x | x | x | x | x |
| [sulfonated (90 styrene/10 N-octyl acrylamide)] sodium salt | x | x | x | 2.0 | x | x | x | x | x |
| [sulfonated (60 styrene/40 butyl acrylate)] sodium salt | x | x | x | x | 2.0 | x | x | x | x |
| [sulfonated (75 styrene/25 butyl acrylate)] sodium salt | x | x | x | x | x | 2.0 | x | x | x |
| [sulfonated (70 styrene/30 methyl methacrylate)] sodium salt | x | x | x | x | x | x | 1.0 | x | x |
| [sulfonated (75 styrene/25 butyl acrylate)] sodium salt | x | x | x | x | x | x | x | 1.0 | x |
| [sulfonated (75 styrene/25 otyl acrylate)] sodium salt | x | x | x | x | x | x | x | x | 1.0 |
| Water (deionized) | 53.0 | 53.0 | 53.0 | 54.0 | 54.0 | 54.0 | 53.0 | 53.0 | 53.0 |
| Ethanol | 45.0 | 45.0 | 45.0 | 45.0 | 45.0 | 45.0 | 45.0 | 45.0 | 45.0 |
| | 100.0 | 100.0 | 100.0 | 100.0 | 100.0 | 100.0 | 100.0 | 100.0 | 100.0 |
| Curl retention (2% solids solution) | | | | | | | | | |
| 30 minutes | 52.0 | 57.4 | 55.2 | 50.2 | 49.7 | 48.6 | — | — | — |
| 120 minutes | 47.1 | 50.3 | 47.4 | 42.4 | 40.7 | 39.4 | — | — | — |

What is claimed is:

1. A process for setting hair comprising the steps of:
   a. applying to the hair an effective amount of a solution of sulfonated polymer selected from the group consisting of a sulfonated polystyrene, a sulfonated interpolymer of styrene with a copolymerizable ethylenically unsaturated comonomer in a proportion of at least 50% styrene, by weight, and a soluble salt of said sulfonated polymers; and a solvent selected from the group consisting of water, ethanol, isopropanol and mixtures thereof, said sulfonated polymers having an average molecular weight of from about 6,000 to about 7,000,000 and being present in an amount of from about 0.1 to about 10.0%, by weight, of the total solution,
   b. fixing the hair in a desired configuration, and
   c. allowing the hair to dry while it is retained in said desired configuration.

2. The process of claim 1 wherein said solution contains a sulfonated polystyrene sodium salt having an average molecular weight between 80,000 and 500,000 and has a pH of from 4.0 to 8.0.

3. The process of claim 1 wherein the ethylenically unsaturated comonomer of said interpolymer is selected from the group consisting of butyl acrylate, octyl acrylate, methyl methacrylate, octyl acrylamide and vinyl pyrrolidone.

4. The process of claim 1 wherein the solution contains an emulsifying agent and an effective amount of an aerosol propellant, and is applied as a quick-breaking foam.

5. The process of claim 1 wherein said sulfonated polymer has an average molecular weight of from about 6,000 to about 300,000 and the solution contains an effective amount of an aerosol propellant therefor and is applied as an aerosol spray.

6. An aerosol hair spray composition in an aerosol container, said composition comprising a solution of a sulfonated polymer selected from the group consisting of a sulfonated polystyrene, a sulfonated interpolymer of styrene with an ethylenically unsaturated comonomer in a proportion of at least 50% styrene, by weight, and a soluble salt of said sulfonated polymers; a solvent selected from the group consisting of water, ethanol, isopropanol and mixtures thereof, and an effective amount of an aerosol propellant therefor; said sulfonated polymers being present in said solution in a concentration of from about 0.1 to 10%, by weight, and having an average molecular weight of from about 6,000 to about 300,000.

7. The aerosol hairspray according to claim 6 wherein said sulfonated polymer is a sulfonated polystyrene sodium salt having an average molecular weight of from about 80,000 to about 300,000, present in a concentration of from about 0.5 to 3.0%, by weight.

8. The aerosol hairspray according to claim 6 wherein the ethylenically unsaturated comonomer of said sulfonated interpolymer is selected from the group consisting of butyl acrylate, octyl acrylate, methyl methacrylate, octyl acrylamide and vinyl pyrrolidone.

* * * * *